(12) United States Patent
Minocha et al.

(10) Patent No.: US 10,902,948 B2
(45) Date of Patent: Jan. 26, 2021

(54) SYSTEMS AND METHODS FOR AUTOMATED PROGRAMMABLE DISPENSING OF MEDICATION

(71) Applicants: Himanshu Minocha, Hopkinton, MA (US); Rohan Minocha, Hopkinton, MA (US)

(72) Inventors: Himanshu Minocha, Hopkinton, MA (US); Rohan Minocha, Hopkinton, MA (US)

(73) Assignees: Himanshu Minocha, Hopkinton, MA (US); Rohan Minocha, Hopkinton, MA (US)

(*) Notice: Subject to any disclaimer, the term of this patent is extended or adjusted under 35 U.S.C. 154(b) by 0 days.

(21) Appl. No.: 16/707,511

(22) Filed: Dec. 9, 2019

(65) Prior Publication Data
US 2020/0234822 A1 Jul. 23, 2020

Related U.S. Application Data

(60) Provisional application No. 62/776,647, filed on Dec. 7, 2018.

(51) Int. Cl.
| | |
|---|---|
| *A61J 7/00* | (2006.01) |
| *G16H 40/67* | (2018.01) |
| *A61J 7/04* | (2006.01) |
| *G07F 7/00* | (2006.01) |
| *G16H 20/13* | (2018.01) |
| *G16H 70/40* | (2018.01) |

(52) U.S. Cl.
CPC ............ *G16H 40/67* (2018.01); *A61J 7/0084* (2013.01); *A61J 7/0454* (2015.05); *A61J 7/0481* (2013.01); *G07F 7/005* (2013.01); *G16H 20/13* (2018.01); *G16H 70/40* (2018.01)

(58) Field of Classification Search
CPC ........ B65D 2583/0418; B65D 83/0454; B65D 83/0409; B65D 25/04; A61J 7/0084; A61J 7/0454
USPC ................................ 221/122, 265, 264, 281
See application file for complete search history.

(56) References Cited

U.S. PATENT DOCUMENTS

| | | | | |
|---|---|---|---|---|
| 5,884,806 | A * | 3/1999 | Boyer ...................... | A61J 7/02 221/13 |
| 6,622,887 | B1 * | 9/2003 | Roediger .............. | A61J 7/0481 221/13 |
| 2002/0070227 | A1 * | 6/2002 | Ferruccio .............. | A61J 7/0481 221/15 |
| 2004/0104241 | A1 * | 6/2004 | Broussard ........... | G07F 17/0092 221/289 |
| 2006/0124502 | A1 * | 6/2006 | Lee ........................ | B65D 25/04 206/539 |
| 2015/0019009 | A1 * | 1/2015 | Feldman ............. | G07F 17/0092 700/237 |
| 2017/0348194 | A1 * | 12/2017 | Duda ....................... | A61J 1/00 |
| 2020/0022876 | A1 * | 1/2020 | Anderson ............. | A61J 7/0454 |

\* cited by examiner

*Primary Examiner* — Timothy R Waggoner
(74) *Attorney, Agent, or Firm* — Goodwin Procter LLP

(57) ABSTRACT

In a medication dispensing system, pills of different medications are stored in different chambers of a pill bottle. An assembly of a non-moving disc having holes corresponding to each chamber, a rotatable disc having a hole for dispensing pills therethrough, and a motor, dispenses the pills according to a prescribed schedule. The motor controls the rotations of the rotatable disc according to a user-specified schedule.

30 Claims, 12 Drawing Sheets

Caretaker Portal

Requests Pending

Drug: OxyContin
Date: 2/12/2018
Time: 7:47 P.M.
[Deny] [Approve]

Drug: OxyContin
Date: 2/12/2018
Time: 7:47 P.M.
[Deny] [Approve]

Drug: OxyContin
Date: 2/12/2018
Time: 7:47 P.M.
[Deny] [Approve]

Drug: OxyContin
Date: 2/12/2018
Time: 7:46 P.M.
[Deny] [Approve]

Drug: OxyContin
Date: 2/12/2018
Time: 7:22 P.M.
[Deny] [Approve]

Drug: OxyContin

Log

Drug: OxyContin
Date: 2/19/2018
Time: 1:1 P.M.
Type: Prescription
Status: Prescription Override DENIED

Drug: OxyContin
Date: 2/19/2018
Time: 12:58 A.M.
Type: Prescription
Status: Prescription Override DENIED

Drug: OxyContin
Date: 2/19/2018
Time: 11:10 A.M.
Type: Prescription
Status: Prescription Override DENIED

Drug: OxyContin
Date: 2/19/2018
Time: 10:44 A.M.
Type: Prescription
Status: Prescription Override

Drug: OxyContin
Date: 2/19/2018
Time: 10:32 A.M.
Type: Prescription
Status: Prescription Override DENIED

Drug: OxyContin

Himanshu Minocha

OxyContin
Scheduled Time: 2:25 P.M.
Last Consumed Date: 2/19/2018
Last Consumed Time: 1:23 P.M.
Dosage: 10 mg
Quantity in Bottle: 5 pills
Weekly Schedule

| Sun | Mon | Tues | Wed | Thurs | Fri | Sat |
|---|---|---|---|---|---|---|
| x | x | x | x | x | x | x |

Advil
Scheduled Time: N/A
Last Consumed Date: 2/17/2018
Last Consumed Time: 9:38 A.M.
Dosage: 20 mg
Quantity in Bottle: 12 pills
Weekly Schedule

| Sun | Mon | Tues | Wed | Thurs | Fri | Sat |
|---|---|---|---|---|---|---|
|  |  |  |  |  |  |  |

FIG. 9

SYSTEMS AND METHODS FOR AUTOMATED PROGRAMMABLE DISPENSING OF MEDICATION

CROSS-REFERENCE TO RELATED APPLICATIONS

This application claims priority to and benefit of U.S. Provisional Patent Application No. 62/776,647, entitled "Systems and Methods for Automated Programmable Dispensing of Medication," filed on Dec. 7, 2018, the entire contents of which are incorporated herein by reference.

FIELD OF THE INVENTION

This disclosure generally relates to techniques for dispensing medication pills and, in particular, to a system having a programmable motor-disc-chamber assembly for dispensing medication pills.

BACKGROUND

Overdosing on drugs can have very dire consequences. It can lead to addiction or dependence on a drug. News media have reported recently that deaths from overdoses of prescription drugs continues to be the leading cause of unintentional death. The bottles in which medications are commonly provided do not have any mechanism that regulates how much of a drug is dispensed at a time. For example, once the cap of the bottle is opened multiple pills can be removed and consumed. Because there is no validation or checking of the prescribed dosage in place, it is relatively easy for someone to overdose intentionally or by mistake. By one estimate, over 1.5 million people are admitted to the hospitals due to misuse of or addiction to prescription drugs. It has also been reported that over 12,000 people died in Massachusetts alone due to accidental overdosing on opioids in the past 15 years. People who suffer from opioid withdrawal typically experience extreme side effects, making addiction to opioids especially dangerous. By limiting the dispensing of drugs according to the prescribed dosage, the number of cases of drug addiction as well as overdoses that may result in death or a serious illness or even death can be reduced.

Intentional or accidental overdosing of addictive drugs is not the only problem associated with the consumption of medications, however. Many people, especially the elderly, are routinely required to take several medications/pills during the day. Some pills are to be taken only in the morning, some only at night, and some twice or three-times a day. Some pills may also need to be taken on the alternate days or only once a week. Some medications/pills are prescription drugs while the others are off-the-counter medications. The combinations of several medications and their respective schedules, which can be quite different, as described above, can make taking these medications in a timely manner not only challenging, but also error prone. Also, if a person does not remember whether she took a certain medication at a certain time, that person may choose not to take another pill to avoid overdosing. This, however, can result in under-dosing.

Some reported automatic pill dispensing devices require a preliminary division of the medication into daily doses, where such doses may be placed into different compartments of a container and then dispensed daily. Not only is this extremely tedious and taxing, for example, to the elderly, but it also undermines an important objective of automatic, controlled dispensing, i.e., avoiding both over- and under-dosing. Because the user himself or herself must divide medication into daily doses, there is a significant risk of error or of intentional misuse. For example, if too much of a particular medication is included in one daily dose, the person taking the medication could overdose on one day. Because the pharmacy generally provides only a limited-day supply at a time, the user may not have adequate dosage of that medication for a different day, resulting in under-dosing on another day. Additionally, these reported devices and systems cannot be controlled by both a person taking the medications and another person, such as a relative or a caretaker. Due to the lack of supervision or double checking by another person, the person taking the medications is highly susceptible to the unintentional errors or misuse discussed above.

Thus, the main problems associated with the known systems include the need to divide the medications into their respective daily doses, the lack of ability to program dispensing of medications according to their respective schedules, and the lack of supervision. These deficiencies can create significant risk of illness or even death due to the addictive nature of some prescription medications, such as opioids. The number of deaths that occurred as a result of overdosing on prescription opioids has quadrupled since 1999. It has been reported that in 2016 alone, over 64,000 people died solely from overdoses on opioids. Even with non-addictive drugs, under-dosing and over-dosing can be harmful. Studies have shown that amongst the elderly, very few regularly take medication as prescribed and in the right doses. Between 40% to 75% of all seniors do not or cannot abide to their prescription medication schedules, according to some reports. Not taking medications as prescribed can cause illnesses or even death.

SUMMARY

Programmatically dispensing the different medications according to their respective prescribed dosages and schedules can alleviate a person's burden and can also minimize or avoid errors in the consumption of medications. Therefore, various embodiments of the Intelligent Cloud Based Medication Dispensing (ICMD) device or system facilitate timely delivery of pills to users. Different kinds of pills can be supplied to a user, where each pill is dispensed according to its respective dosage (e.g., number of pills to be dispensed at a certain time), and schedule (e.g., once, twice, or thrice a day, on alternate days, once a week, in the mornings only, at night only, etc.). A user specific and medication specific dosage and the dispensing schedule can be provided to the device by the user or a trusted caretaker. The dosage and schedule may also be derived from the drug labels of databases accessed by the ICMD system. Various embodiments of the ICMD device also allow a user to request additional dosages, either via a user portal/app run on a user device, or directly from the device. Such requests may be authorized by another person—a designated caretaker—via a portal/app provided to the caretaker. This can help avoid or mitigate both the under and over-dosing and misuse of medications.

Accordingly, in one aspect, a device is provided for dispensing medication pills. The device includes a first chamber for storing pills of a first type, and the first chamber has an inlet for receiving pills of the first type. The device also includes an enclosure disk that encloses the first chamber and has a first hole providing an outlet from the first chamber. In addition, the device includes a rotatable disk coupled to a motor, where the rotatable disk has a dispensing hole that can be aligned with the first hole in the enclosure disk. Moreover, the device includes a local controller for initiating a rotation of the rotatable disk and for controlling an angle of rotation of the rotatable disk such that, at a first angle of rotation used by the local controller, an overlap between the first hole in the enclosure disk and the dispensing hole in the rotatable disk corresponds to a size of a pill of the first type. When the two holes are thus aligned, a pill of the first type may be dispensed from the device.

The inlet of the first chamber may include a spring-loaded lid. The local controller may be programmed to initiate the rotation of the rotatable disk according to one or more of: a first time of the day, a first frequency of dispensing pills of the first type, or an administer override. In some embodiments, the device includes a second chamber for storing pills of a second type, where the second chamber has an inlet for receiving pills of the second type. In these embodiments, the enclosure disk encloses the second chamber and has a second hole providing an outlet from the second chamber, and the dispensing hole of the rotatable disk can be aligned with the second hole in the enclosure disk. The local controller may configured for controlling the angle of rotation of the rotatable disk such that, at a second angle of rotation used by the local controller, an overlap between the second hole in the enclosure disk and the dispensing hole in the rotatable disk corresponds to a size of a pill of the second type. When the second hole in the enclosure disk and the dispensing hole in the rotatable disk are thus aligned, a pill of the second type may be dispensed from the device.

The inlet of the second chamber may include a spring-loaded lid. The local controller may be programmed to initiate the rotation of the rotatable disk according to one or more of: a second time of the day, a second frequency of dispensing pills of the second type, or an administer override. In some embodiments, the local controller is programmed to cause a rotation of the rotatable disk, while the dispensing hole passes over the first hole in the enclosure disk, at an angular speed at which a pill is not dispensed through the first hole and the dispensing hole when the two holes are aligned.

In some embodiments, the local controller includes a processor and a communication interface or a user interface for receiving one or more of a set of control parameters or a set of instructions, for programming the local controller. The set of control parameters may include one or more of: a pill identifier; a pill type, a set of one or more times of the day at which a pill of a specified type is to be dispensed, a frequency of dispensing pills of the specified type, or a size of a pill of the specified type. The processor may be programmed to compute the first angle of rotation based on, at least in part, the size of the pill of the specified type.

In some embodiments, the pill identifier is specified via the communication interface, and the pills of the specified type include pills identified by the pill identifier. The local controller may be programmed to: query a database using the pill identifier; and determine, using information received from the database, one or more of: (i) the set of one or more times of the day at which a pill of the specified type is to be dispensed, (ii) the frequency of dispensing pills of the specified type, or (iii) the size of a pill of the specified type.

In some embodiments, the set of instructions includes a schedule for initiation of rotation of the rotatable disk, and the set of control parameters includes the first angle of rotation. The communication interface may be adapted to receive one or more of: a user acknowledgment that a dispensed pill was consumed, or a user request to dispense a pill of the first type. The communication interface may be programmed to seek authorization prior to dispensing the pill, upon receiving the user request to dispense a pill. The device may include an alarm configured to indicate one or more conditions including: a time at which a pill of the first type would be dispensed is approaching; a pill of the first type has been dispensed; or a user-specified time has elapsed after a pill of the first type was dispensed. The pills of the first type may be selected from the group consisting of: opioids, prescription medication; or non-prescription medication.

In another aspect, a user device is provided that includes a remote controller in electronic communication with a local controller of a pill-dispensing device having a pill chamber, an enclosure disk, and a motorized rotatable disk. The local controller is programmed to initiate a rotation of the rotatable disk according to one or more of: a time of the day at which a pill is to be dispensed, a frequency of dispensing pills, a pill size, a total number of pills initially placed in the chamber, a pill identifier, or an administer override. The remote controller is programmed to transmit to the local controller one or more of: the time of the day at which the pill is to be dispensed, the frequency of dispensing pills, the pill size, the total number of pills initially placed in the chamber, or the pill identifier.

The remote controller may be programmed further to: receive from the local controller of the pill-dispensing device an authorization request for dispensing a pill, provide, in response to the received request, a signal to a user (e.g., an administrator), and transmit, according to a user input, the administer override to the local controller. Additionally or in the alternative, the remote controller may be programmed to: receive from the local controller of the pill-dispensing device information about dispensing of pills, where the information includes one or more of: a number of pills dispensed during a specified time period, a number of pills remaining in the chamber, a number of authorization requests for dispensing the pill, or the number of administer overrides. The remote controller may also be programmed to or configured to display the received information.

In another aspect, a method is provided for dispensing medication pills. The method includes initiating, at a pre-selected first time and according to a first angle of rotation, a rotation of a rotatable disk of a medical pill dispensing device, where the rotation causes, at the first angle of rotation, an overlap between a first hole in an enclosure disk of the medical pill dispensing device and a dispensing hole in the rotatable disk. As such, a pill of the first type can be dispensed through the overlapping or aligned first hole in an enclosure disk and the dispensing hole in the rotatable disk. The method also includes limiting a speed of rotation such that a medical pill of the first type is dispensed from the device when the first hole in the enclosure disk and the dispensing hole in the rotatable disk are aligned. The method further includes stopping the rotation of the rotatable disk after the dispensing hole in the rotatable disk passes over the first hole in the enclosure disk.

In some embodiments, the method further includes initiating, at a pre-selected second time and according to a second angle of rotation, a rotation of the rotatable disk of the medical pill dispensing device that causes, at the second angle of rotation, an overlap between a second hole in the enclosure disk of the medical pill dispensing device and the dispensing hole in the rotatable disk. In these embodiments, the method also includes limiting a speed of rotation such that a medical pill of a second type is dispensed from the device when the second hole in the enclosure disk and the dispensing hole in the rotatable disk are aligned, and stopping the rotation of the rotatable disk after the dispensing hole in the rotatable disk passes over the second hole in the enclosure disk.

In some embodiments, during operation, when at a second angle of rotation, the dispensing hole in the rotatable disk is aligned with a second hole in the enclosure disk, the method includes maintaining the speed of rotation such that a medical pill of the second type is prevented from being dispensed from the device when the second hole in the enclosure disk and the dispensing hole in the rotatable disk are aligned. Thus, the dispensing hole would pass over the second hole in the enclosure disk at a speed high enough that after those two holes become aligned, they would become dis-aligned in a short interval of time (e.g., a few milliseconds), where the time required for a pill of the second type to be dispensed from those two holes when aligned is longer than the short interval.

In some embodiments, the method includes repeating the initiating, limiting, and stopping steps at a pre-selected third time such that another medical pill of the first type is dispensed from the device at the third time.

In another aspect, a method is provided for controlling dispensing of medication pills from a pill-dispensing device having at least one pill chamber, where each chamber is designated to a particular type of pills. The method includes receiving a first chamber identifier (e.g., Chamber_A, Chamber_III, etc.), identifying a first chamber designated for storing medication pills of a first type. The method also includes obtaining a size of the pills of the first type, and computing a first angle of rotation for a rotatable disk of the pill-dispensing device. The first angle is relative to a specified origin of the rotatable disk and is based on: (i) a total number of chambers in the device, (ii) the first chamber identifier, or (iii) the size of the pills of the first type. The method also includes selecting an angular speed of rotation for the rotatable disk when the rotatable disk is rotated through the first angle. If the speed is sufficiently slow, a pill of the first type would be dispensed when a dispensing hole in the rotatable disk is aligned with a first hole in an enclosure disk, where the first hole corresponds to the first chamber. Otherwise, it the speed is greater than a certain threshold, a pill of the first type would not be dispensed even when the dispensing hole in the rotatable disk is aligned with the first hole in an enclosure disk, for a short duration (e.g., for a few milliseconds). Thus, in various embodiments, the selected angular speed of rotation allows dispensing of the pill from the pill-dispensing device, or prevents dispensing of the pill from the pill-dispensing device.

The size of the pills of the first type may be specified as one or more of a length of the pills of the first type, a width of the pills of the first type, or a diameter or the pills of the first type. Obtaining the size of the pills of the first type may include receiving the size of the pills of the first type, e.g., from a user, via a user interface. Alternatively, obtaining the size of the pills of the first type may include receiving a first pill identifier identifying the pills of the first type, and accessing a database using the first pill identifier, and receiving from the database the size of the pills of the first type. The database may be a local database included with the pill-dispensing device, or a database at a pharmacy, or a public database such as a Food and Drug Administration (FDA) database.

In some embodiments, the steps of receiving, obtaining, computing, and selecting are performed at a remote controller. In these embodiments, the method may include transmitting the first angle of rotation and the angular speed of rotation to a local controller included in the pill-dispensing device. These parameters may be computed by the remote controller or a computing device (e.g., a smart phone, tablet computer, laptop or desktop computer, etc.) associated with the remote computer. In some other embodiments, the step of obtaining the size of the pills of the first type is performed at a remote controller, and the method may include transmitting the size of the pills of the first type to a local controller included in the pill-dispensing device. The local controller and/or a processor in the pill-dispensing device may then compute additional control parameters such as the first angle of rotation and the angular speed of rotation.

In some embodiments, the method includes receiving a second chamber identifier that identifies a second chamber designated for storing medication pills of a second type, and obtaining a size of the pills of the second type. The method may further include computing a second angle of rotation for the rotatable disk of the pill-dispensing device, the second angle being relative to the specified origin of the rotatable disk and being based on: (i) the total number of chambers in the device, (ii) the second chamber identifier, and (iii) the size of the pills of the second type.

According to another aspect, a method is provided for operating a pill-dispensing device. The method includes: providing medication pills of a first type in a first chamber of the pill-dispensing device, inputting via a user interface an identifier or a size of the pills of the first type, and inputting via the user interface a first schedule of delivery for the pills of the first type. The method also includes receiving an indication that the pill-dispensing device is configured to dispense pills of the first type according to the first schedule.

Inputting the size may include inputting a length of the pills of the first type, a width of the pills of the first type, or a diameter of the pills of the first type. Inputting the first schedule may include specifying: a frequency at which the pills of the first type are to be dispensed, and one or more times of the day at which the pills of the first type are to be dispensed. The frequency can be specified as daily, twice a day, three times a day, every four hours, on every alternate day, once a week, etc. The frequency may also include the number of pills to be dispensed at each time of dispensing, such as, e.g., one pill in the morning, or two pills at night, etc. The one or more times of the day may be specified as in the morning, in the evening, in the afternoon, at 8 am, at 2 pm, at 9 pm, or as combinations of such specifications.

The user interface may include a local user interface, such as a key pad or a touch screen included with the pill-dispensing device. Alternatively, the user interface may include a remote user interface, such as a user app executed on a smart phone, tablet computer, laptop or desktop computer, etc. In embodiments where the user interface includes a remote user interface, the method may include receiving a request for out-of-schedule dispensing of a pill of the first type. Such request may be received via another user interface, e.g., an interface included with the pill-dispensing device or via another user app executed on a different smart phone, another tablet computer, another laptop, or another desktop computer, etc. The method may also include transmitting a signal from the remote user interface to dispense out-of-schedule a pill of the first type. The method may further include maintaining a record over a specified time window (e.g., a day, a week, a month, etc.) of requests for out-of-schedule dispensing of the pills of the first type.

In some embodiments, the method includes: providing medication pills of a second type in a second chamber of the pill-dispensing device; inputting via the user interface an identifier or a size of the pills of the second type; and inputting via the user interface a second schedule of delivery for the pills of the second type. Additionally, the method may include receiving an indication that the pill-dispensing device is configured to dispense pills of the second type according to the second schedule. The second schedule may overlap, at least partially, the first schedule. For example, in the morning only a pill of the second type may be dispensed, but at night both a pill of the first type and a pill of the second type may be dispensed. Alternatively, the first and the second schedules may be non-overlapping.

BRIEF DESCRIPTION OF THE DRAWINGS

Various aspects of the claimed invention will become more apparent in view of the attached drawings and accompanying detailed description. The embodiments depicted in the drawings are provided by way of example, not by way of limitation, wherein like reference numerals/labels generally refer to the same or similar elements. In different drawings, the same or similar elements may be referenced using different reference numerals/labels, however. The drawings are not necessarily to scale, emphasis instead being placed upon illustrating aspects of the invention. In the drawings:

FIG. 9 illustrates the information displayed at a remote controller and/or a remote user interface, according to one embodiment;

DETAILED DESCRIPTION

Hardware

Figure 1:
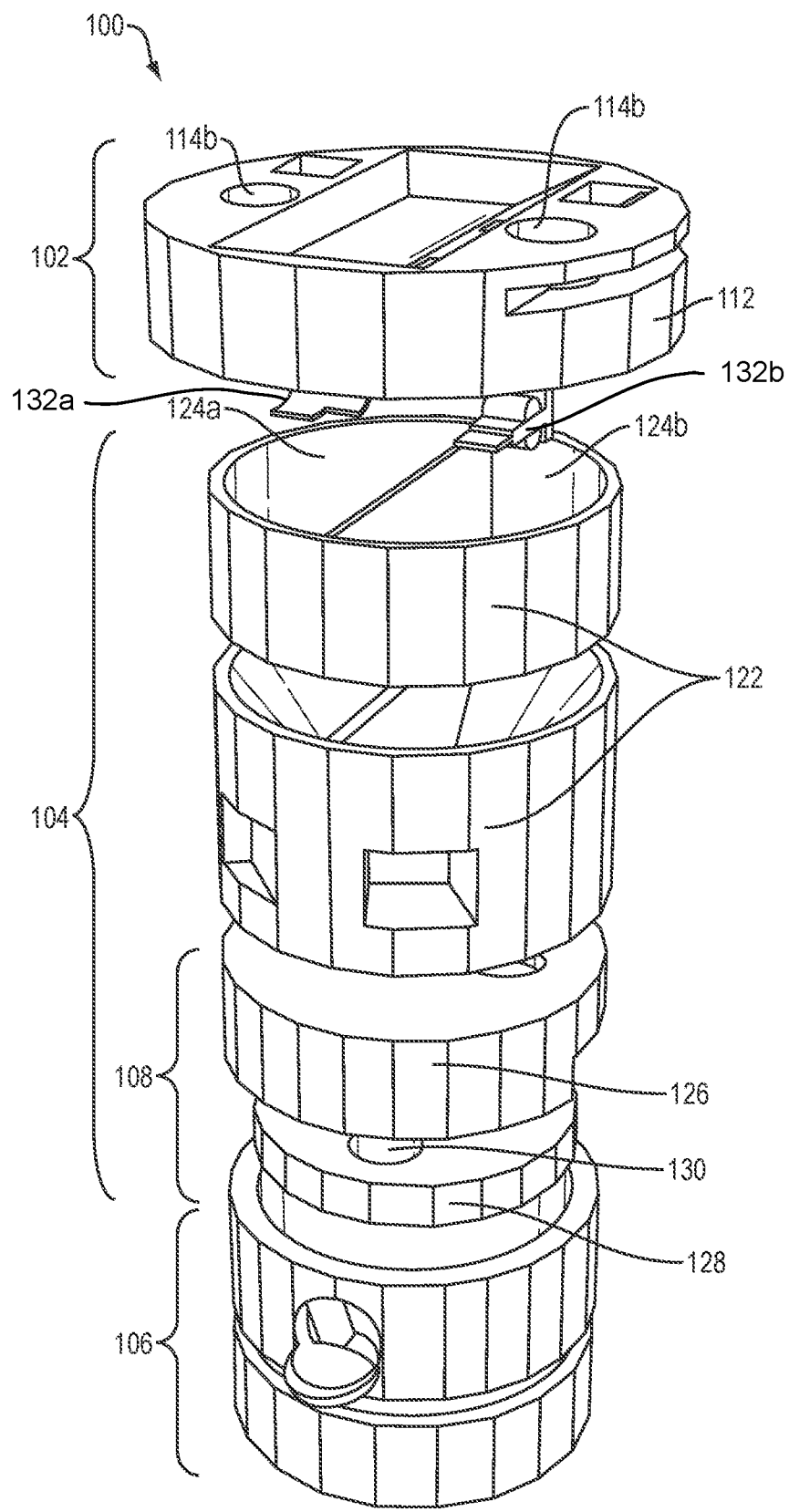
FIG. 1 depicts a pill-dispensing device, according to one embodiment.

Embodiments of the ICMD device include several layers that are designed to dispense medications accurately and in an optimized way with respect to quantity and timing. With reference to FIG. 1, in various embodiments of the ICMD device 100, there are three main subsections: a cap layer/section 102, a feeding layer/section 104 having a bottle 122, having one or more chambers 124a, 124b for one or more medications, and the layers 106 pertaining to the motor functionality. In some embodiments, the dispensing device includes seven layers. The entire device may also be referred to as a bottle.

Figure 2:
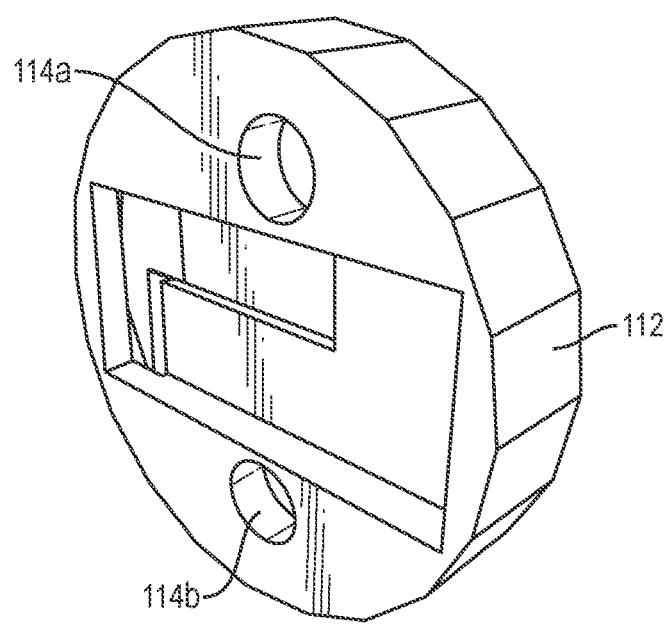
FIG. 2 depicts a cap of the pill-dispensing device shown in FIG. 1.
Figure 6:
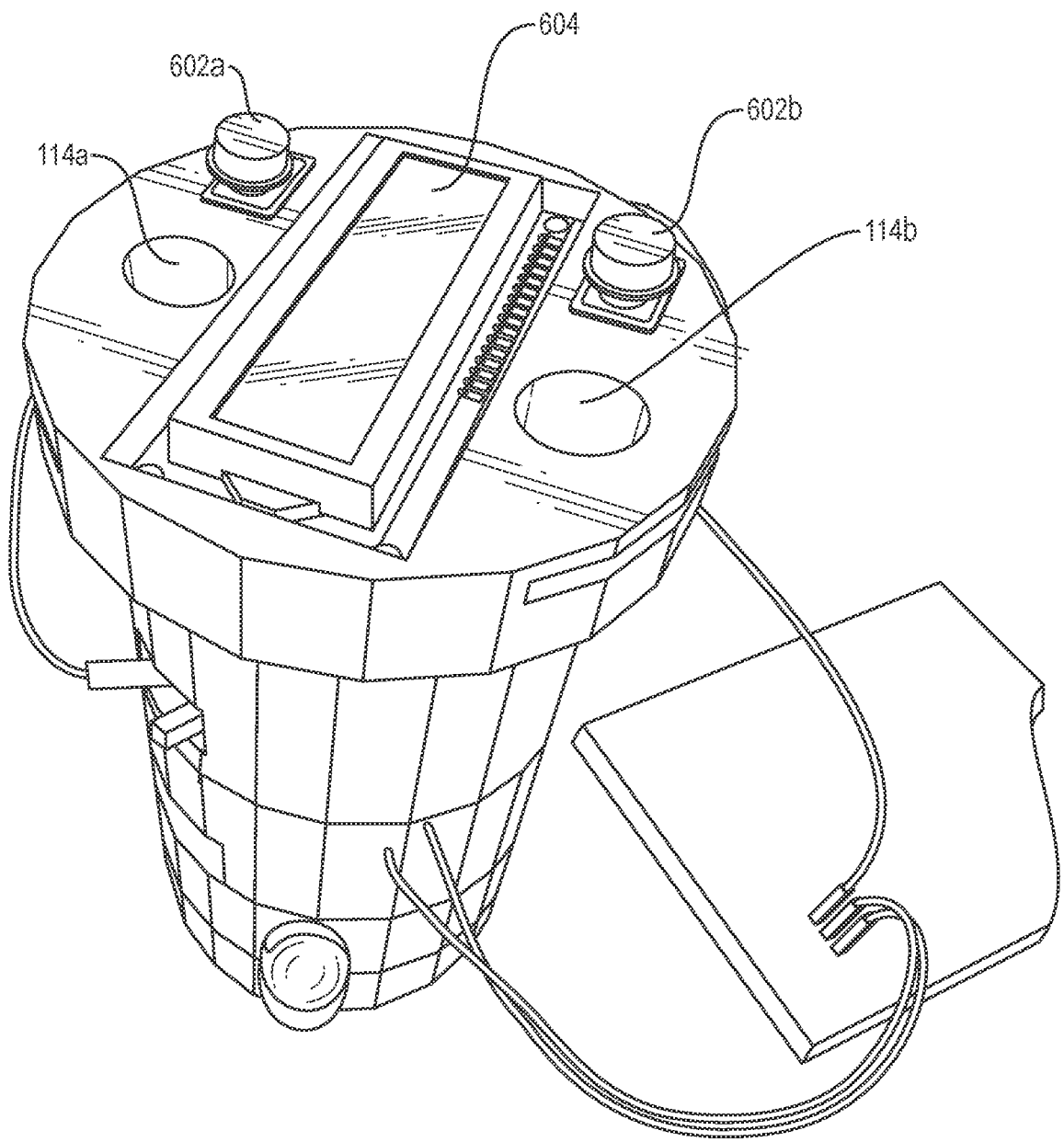
FIG. 6 depicts a pill-dispensing device, according to one embodiment.

The uppermost layer includes a cap 112. The cap may house one or more buttons (602am 602b, as shown in FIG. 6) and/or a display screen (604, also shown in FIG. 6), and/or one or more LEDs. In one embodiment, depicted in FIGS. 1 and 2, the cap 112 has two holes 114a, 114b through which medication is placed into the respective chambers 124a, 124b of the bottle 122. In order to prevent the user from manually taking out the medication, each hole/opening may be closed using a spring-loaded lid/door 132a, 132b, respectively. The spring-loaded doors 132a, 132b may open in only one direction, i.e., into the chamber, securing medication inside the bottle. Thus, medication may only be placed into the bottle but cannot be easily removed, unless dispensed as scheduled/prescribed. The cap contains two separate holes/openings that are associated with two different chambers/compartments of the bottle where each chamber can hold a different medication. Either medication can be a prescription or a non-prescription medication, and the two medications may be dispensed according to the same or different schedules.

For the convenience of discussion, the description below generally refers to this particular embodiment, i.e., one having two chambers in the bottle, but it should be understood that this embodiment is not limiting. Embodiments in which the cap includes only one hole that is associated with only one chamber in the bottle is contemplated. Likewise, embodiments in which the cap includes three, four, five, or more holes, and the bottle includes a corresponding number of chambers, where each chamber is associated with a respective hole/opening in the cap, are also contemplated. The operation of the motor is controlled according to the number of chambers in the bottle and the respective dispensing schedules of the medications placed in those chambers, as described below. In general, the ICMD device allows users to store several different types of medication in one single unit.

In an ICMD device, a medication is placed in a cylindrical container (also called a pill bottle) 122 that may be partitioned into two or more chambers (e.g., chambers 124a, 124b) using partitions running across the diameter of the pill bottle or running from a central axis of the pill bottle to the surface thereof. These partitions may run the entire length of the pill bottle. Through the corresponding holes in the cap, different types of pills are placed in different chambers. As such, once disposed in the respective chambers, the medications do not contact medications in the other chambers, minimizing the risk of contamination of mixing of different medications. This can ensure that particularly volatile medications are not mixed with other prescription or non-prescription medications.

Figure 3:
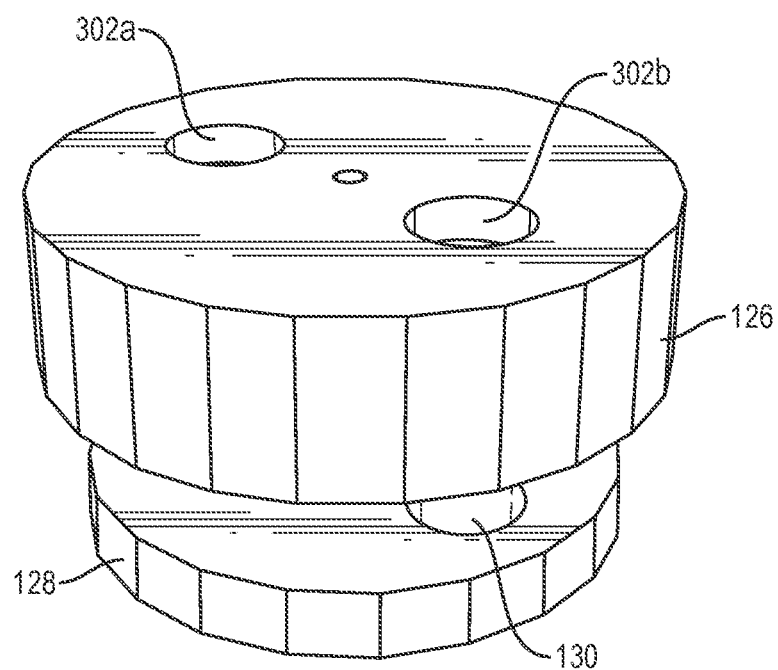
FIG. 3 depicts an assembly of an enclosure disc and a rotatable disc of the pill-dispensing device shown in FIG. 1.

The bottom of the pill bottle is closed using a sublayer/subsection called an enclosure layer 108 that includes a nonmoving disc (also called an enclosure disc 126), as shown in FIGS. 1 and 3. The enclosure disc 126 has the same number of holes/openings as the number of chambers in the pill bottle, where each hole/opening (e.g., 302a, 302b) corresponds to a respective chamber (124a, 124b). The pills placed in a chamber can pass through the corresponding hole of the enclosure disc. As shown in FIGS. 1 and 3, the enclosure layer/section 108 also includes a spinning disc or a rotatable disc 128 that is placed beneath the enclosure disc. The spinning disc has only one hole/opening (also called a dispensing hole) 130. When that hole is not aligned with any of the holes in the enclosure disc, no pills are dispensed.

When the hole of the spinning disc is aligned with a particular hole in the enclosure disc, pills from the corresponding chamber would be dispensed. In order to dispense only one pill at a time from a selected chamber, the speed and the angle of rotation of the spinning disc are controlled, as described below. Once the spinning disc dispenses a single pill, the medication is dropped down to a sloping surface, directing the medication towards a lip, which allows the user to quickly, and easily retrieve the medication once it has been dispensed.

Figure 4:
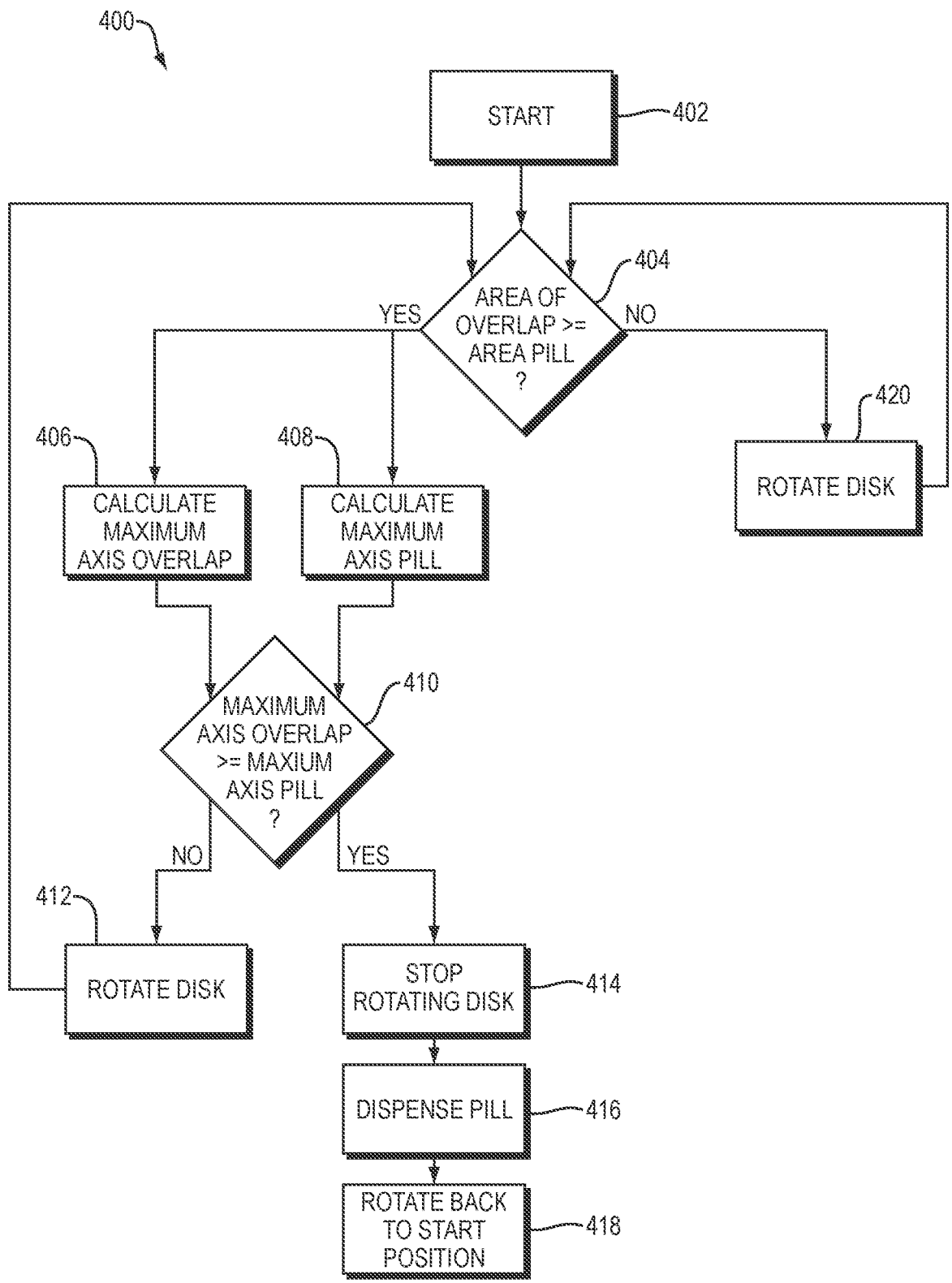
FIG. 4 shows a process for computing various angles used in the operation of a pill-dispensing device, according to one embodiment.
Figure 5A:
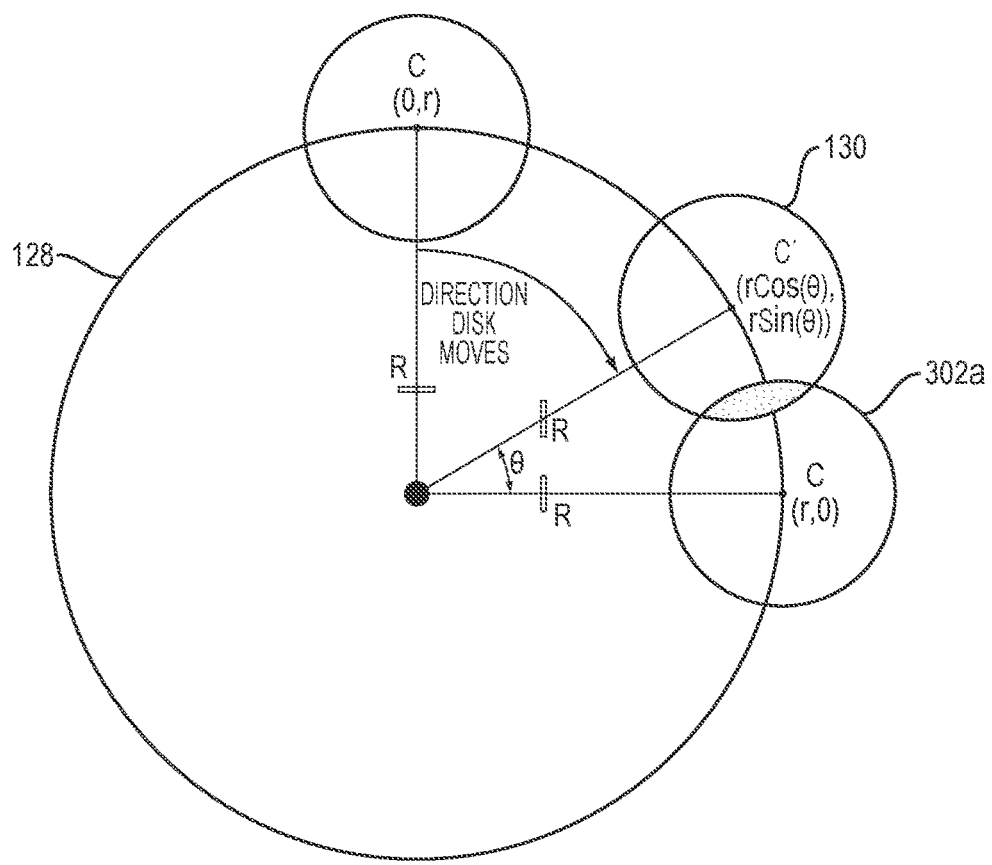
FIGS. 5A and 5B schematically illustrate movement of a rotatable disc and alignment of holes, according to one embodiment.
Figure 5B:
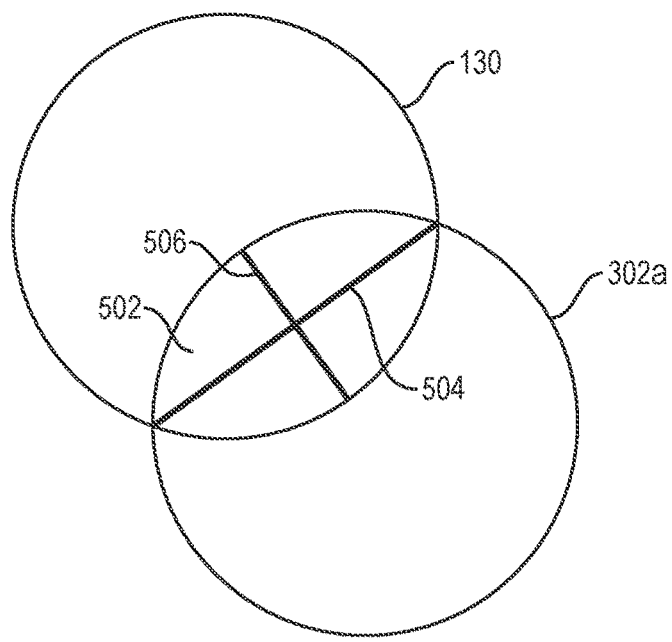

Either upon request, or according to a preset schedule, one or more medications will be dispensed from one or more chambers. Upon request or at a scheduled time, a spinning disc beneath the pill bottle is rotated precisely according to a certain angle so that one single pill is dispensed from a selected chamber of the pill bottle. The precise rotation of the spinning disc mechanism ensures that no more medication is dispensed aside from the pre-scheduled or requested medication. The motor uses precise turns to enable only a single pill to be dispensed. With reference to FIG. 4, a mathematical function is used by a process 400 to determine the rotation in degrees that the motor must be rotated causing the spinning disc to be rotated by a precise selected angle which, in turn, provides an opening through the non-moving enclosure disc and the spinning disc that is just wide enough to accommodate the size/dimensions of the pill to be dispensed. This mathematical function treats the dispensing hole 130 in the spinning disc 128 and a particular hole (e.g., 302a) in the enclosure disc 126 as two separate overlapping circles, each of which is graphed on a Cartesian plane, as shown in FIGS. 5A and 5B.

With reference to FIG. 4, the process may select an angle θ in the beginning (step 402). In some embodiments, all chambers are of the same size. As such, from a refence or rest place (also called origin) of the rotatable disc 128, the respective holes of the enclosure disc 126 are at angles (in degrees)

$$\frac{360}{N}, 2 \times \frac{360}{N}, 3 \times \frac{360}{N},$$

and so on, where N is the number of chamber. Thus, if the rotatable disc 128 were rotated from the origin through an angle (in degrees)

$$k \times \frac{360}{N},$$

the center of the dispensing hole 130 and the center of an enclosure-disc hole associated with the k-the chamber may be aligned. If the rotatable disc 128 were rotated from the origin through an angle (in degrees) less than $$k \times \frac{360}{N}$$

by a threshold, e.g., less by 30°, 20°, 8°, 5°, etc., dispensing hole 130 and the enclosure-disc hole associated with the k-the chamber may be tangential. As such, by rotating the disc 128 further, the two hole would begin to overlap. In step 402, the angle θ can thus be selected based on the number of chambers and a threshold which, in general, is based on the radius or diameter of the dispensing hole 130. If the different chambers are of different sizes, the initial value of the angle θ can be selected by taking into account the dimensions of the chambers.

Once the holes begin to overlap, the process may then determine whether the area of the overlapping region (shown as area 502 in FIG. 5B) is greater than the area of the pills in the k-the chamber. If not, the rotation of the disc 128 may continue (step 420). Otherwise, the process 400 may compute the lengths of the major and/or minor axes of the overlapping region 502 (FIG. 5B; major and minor axes are shown as 504, 506 in FIG. 5B) in step 406. The process 400 may obtain or compute the major (longer) and minor (shorter) axes of the pills in the k-the chamber, as well (step 408). If the larger of the major and minor axes of the overlapping region 502 (FIG. 5B) is determined not to be greater than or equal to the larger of the major and minor axes of the pills in the k-the chamber (step 410), the pill would not be dispensed even though the two holes are overlapping. As such, the rotation of the disc may be continued (step 412).

If the condition evaluated in step 410 is true, however, the rotation of the rotatable disc 128 may be slowed down substantially or may even be stopped momentarily (step 414), and the angle θ may be set to the angle through which the disc 128 is rotated. The revised value of angle θ may be associated with the k-the chamber in step 414. A pill from the k-the chamber would then be disposed (step 416) and the disc 128 may then be rotated back to the rest position (origin) (step 418). Rotating the disc back to the origin can be accomplished by reversing the direction of rotation or by continuing rotation in the same direction so as to complete a full rotation. Alternatively, the disc 128 may be rotated further, in a similar manner as described above, so that a pill from another chamber is dispensed. To this end, the angle θ may be computed not relative to the origin but to the current orientation of the disc 128.

In some embodiments, if a pill from a particular chamber is not to be dispensed when the hole in the enclosure disc that corresponds to that particular chamber and the dispensing hole 130 align, the motor rotating the rotatable disc may be operated at a relatively high speed, e.g., 30, 50 RPM, etc. On the other hand, if a pill from that chamber is to be dispensed, the motor may be operated at a relatively slow speed, e.g., 25 RPM, 15 RPM, or lower.

In general, in the process 400, the following measurements are calculated: area of overlap between the dispensing hole and a particular hole in the enclosure disc, where that hole corresponds to a particular chamber, and the lengths of the major and minor axes of the overlapping region. These measurements are compared with the dimensions of the pills designated to the particular chamber to determine whether the angle of rotation would dispense a pill from that chamber. Once that angle is determined (revised θ, as described above), it may be stored in memory for repeated dispensing, until the type of pills designated to the corresponding chamber is changed.

In another embodiment, various computations are performed before moving the motor and, once performed, the computed angles may be stored in memory for subsequent use, without having to repeat the computations for dispensing pills of a particular type from a particular chamber. These computations may be performed as follows:

Let d represent the distance between the centers of two holes, i.e., the dispensing hole and the enclosure-disc hole corresponding to the chamber from which a pill is to be dispensed. Let r represent the radius of both holes. The major axis and the area of overlap are then derived as:

$$majorAxis = \frac{1}{d} * \sqrt{4d^2 * r^2 - (d^2)^2}$$

$$\text{Area Of Overlap} = 2r^2\left(\frac{d}{2r}\right) - \frac{d}{2}\sqrt{4r^2 - d^2}$$

These two computations assist the controller of the device in determining whether a pill from a particular chamber will pass through the two holes when they are aligned, i.e., when the two holes overlap such that: (i) the major axis of the overlapping region is greater than or equal to the maximum (or longer) axis of the pill, and (ii) the area of the pill is less than or equal to the area of the overlapping region. In this case, the rotation of the rotatable disc can be slowed down or stopped. Otherwise, the rotatable disc may be rotated, e.g., in fixed angular increments, where each revised value of θ corresponds to a different value of d. The computations above can accommodate the cases where the radii of the two holes are different.

If the overlapping hole size is less than one of the dimensions of the actual pill, the angle θ can be decremented, e.g., by some constant c, and the overlapping hole size can be computed again such that the overlapping hole size matches the actual pill size. In this context, the sizes are considered to match when in each of X and Y dimensions, the corresponding dimension of the overlapping hole is approximately (i.e., within 0.5%, 1%, 2%, 5%, 10%, 20%, etc.) equal to the pill size in the corresponding dimension.

In order to dispense more than one medications in a selective manner, the device uses variable speed. Because a large number of consumers take several medications but according to different schedules, this is a useful if not a necessary feature. By using variable speed, the hole of the rotating disc moves past the holes of the enclosure disc rapidly, preventing dispensing of more than one pill at a time. In general, the hole of the spinning disc starts at a pre-determined neutral position, which is referred to as the "origin," which is attributed an angle measure of 0 degrees. At the neutral position, there is no overlap between the holes of the spinning and enclosure discs. Any amount of medications can be placed into a chamber of the bottle with some constraints, as described below. In one example, the starting position of the spinning disc is 0 degrees, and three holes in the enclosure disc, denoted H1, H2, and H3, are located at 90 degrees, 180 degrees, and 270 degrees, respectively. These angles are illustrative only, and other angles are contemplated. The hole in the spinning disc is denoted Hs.

In order to dispense a pill through the hole H1, the spinning disc may be rotated, as described above, up to an angle where the overlap between the holes Hs and H1 is approximately equal to the size of the pill to be dispensed through the hole H1. Thereafter, the speed of rotation is increased such that no more than one pill would be dispensed through the hole H1. If a pill is also to be dispensed through the hole H2, the speed of rotation is slowed after there is no overlap between the holes Hs and H1, and then the disc is rotated up to an angle where the overlap between the holes Hs and H2 is approximately equal to the size of the pill to be dispensed through the hole H2. Thereafter, the speed of rotation is increased again, such that no more than one pill would be dispensed through the hole H2. A similar process is repeated to dispense a pill through the hole H3.

If a pill is not to be dispensed through the hole H2, however, and, instead, pills only from the holes H1 and H3 are to be dispensed, the spinning disc is rotated at a high speed such that the hole Hs passes over the hole H2 at a speed that is high enough that no pill from the hole H2 is dispensed. The rotation of the disc is slowed once there is no overlap between the holes Hs and H2, so that a pill from the hole H3 can be dispensed, as described above. If no pills from the holes H2 and H3 are to be dispensed and, instead, two pills from the hole H1 are to be dispensed, the spinning disc is rotated at a high speed such that the hole Hs passes over the hole H3 as well, at a high speed, without allowing a pill from that hole to be dispensed. The rotation of the disc is slowed once there is no overlap between the holes Hs and H3, so that a second pill from the hole H1 can be dispensed.

This method can be used to have any number of chambers/compartments (denoted n) in the pill bottle. The only limiting factor is the space available in the pill bottle for each chamber/compartment, which depends on the size of the n holes in the enclosure disc, where each hole must be separated from the other holes. The size of each hole in the enclosure disc is generally large enough to allow the largest pills to pass therethrough. In general, by increasing the bottle size it is possible to provide several compartments as needed, allowing dispensing of several different medications from a single bottle. According to the technique described above, the motor can be operated to dispense pills from one or more of n compartments/chambers, where n can be 1, 2, 3, 4, 5, or more. In some embodiments, the holes in the non-moving enclosure disc are spaced evenly, i.e., the angle between the adjacent holes in the non-moving enclosure disc is approximately (within a tolerance of 0.5%, 1%, 5%, 20%, 20%, etc.) 360/(n+1), where n is the number of compartments/chambers and also the number of holes in the enclosure disc. For example, with three compartments/chambers, from the initial position of the rotating disc hole, dispensing holes, i.e., the holes in the enclosure disc may be placed at 90-degree intervals.

Various embodiments of the ICMD device utilize several technologies in order perform specific tasks. For example, a motor, a motor controller, a microprocessor, and a wireless communication module (e.g., an HM10 Bluetooth™ module) may be utilized in order to enable the functionality of dispensing medication at pre-designated times.

In various embodiments, the ICMD device includes audio-visual feedback mechanisms. The three technologies that may be used as a part of the audio-visual feedback mechanisms include an LCD screen, LED lights, and speakers. Audio-visual feedback may be provided under specific circumstances, to provide various notifications to the users. For example, feedback may be provided when it is time to take a medication, while a pill is dispensed, and/or if a dosage is missed. In some embodiments, the user is expected to press a button on the cap to acknowledge and indicate that the user collected and consumed a dispensed pill. If the acknowledgment button is not pressed after a certain time interval (e.g., 5 min, 15 min, 30 min, 1 hr. etc.) has passed after the pill was dispensed, an audio-visual feedback indicating a missed dosage may be provided.

A caretaker or the user may choose the time interval after which the missed dosage feedback is provided. In some embodiments, the feedback includes a beeping emitted from the speaker. In some embodiments, an auditory feedback is given in intervals of 1 second with a half second pause in between each interval. This pattern of the speaker is repeated for approximately 6 seconds. The speaker is also implemented to provide a medium of feedback to those who are visually impaired and may not recognize the visual feedback. Audio-visual feedback mechanisms may also include the use of LED lights.

With reference to FIGS. 1 and 6, in some embodiments, the cap 112 includes buttons 602a, 602b that allow a user to interact with the ICMD device. In some embodiments, one button is associated with each chamber, allowing the user to request a pill from that chamber. The user can press this button if the user has missed his or her daily dosage (e.g., if a dispensed pill was lost), or if the user requires an additional dosage, i.e. a dosage in addition to the programmed, regular prescription dosage. In various embodiments, the ICMD device treats a request for an additional dosage as a system override. Therefore, the device sends an approval request to a caretaker, and dispenses the additional dosage only upon receiving approval from the caretaker. In some embodiments, two buttons correspond to each chamber, where the second button is used to acknowledge that the use consumed a pill that was dispensed from that chamber. In some embodiments, a button that is common to all the chambers is used for acknowledgment.

Figure 7:
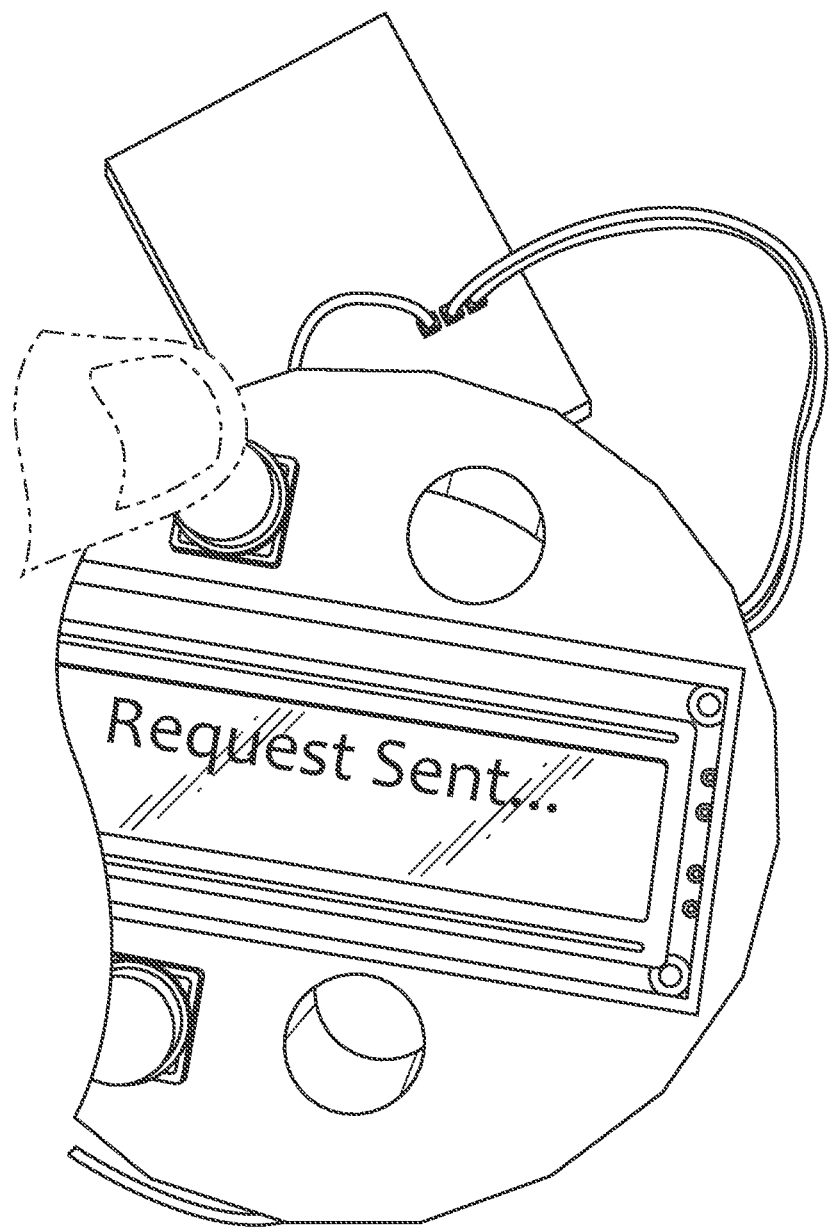
FIG. 7 depicts a cap and a local user interface of a pill-dispensing device, according to one embodiment.

Similarly to the buttons, a respective LED may correspond to each chamber. In some embodiments, after a pill is dispensed from a chamber if the user does not acknowledge taking that pill, the LED corresponding to that chamber starts to flash, e.g., similar to the beeps of the speaker, alerting the user of the missed dosage. With reference to FIGS. 6 and 7, in some embodiments, an LCD screen 604 provides feedback in a similar manner, but the LCD screen can also provide textual information to the user, e.g., information about the medication. The ICMD device is capable of performing several actions, and the LCD screen can provide feedback by reaffirming and verifying the user's action. For example, if the user were to press a button to request additional dosage, the LCD screen may display the messages "Request Sent," "Request Approved," "Request Denied," etc.

In addition to the LEDs and/or the speakers, or in the alternative, the LCD screen can display a message notifying the user of a missed dosage. The LCD screen may also be used to display relevant information pertaining to the medication that is currently being dispensed. For example, in some embodiments, when the user or a caretaker programs an ICMD device to dispense a certain medication, a Food and Drug Administration (FDA) database is queried to find common warnings and instructions for the specific medication. That information may be displayed to the user via the LCD screen when that specific medication is dispensed.

Various embodiments of the ICMD device include an app that can be executed on a mobile device (e.g., a smart phone, tablet, smart watch, etc.) and/or on a computer or laptop. The app can be used to control, program, and/or operate the ICMD device, and/or to provide alerts and/or other information to the users such as the information provided by the audio-visual feedback system. Although the number of people, including the elderly, using smartphones and other mobile devices is increasing, some users may prefer not to operate the ICMD device using an app or may not have access to a mobile device. Therefore, to such users, the audio-visual feedback mechanisms described above can provide useful information without relying on an accompanying software app.

In various embodiments, the software app is used to program an ICMD device. In particular, a user or a caretaker may select a chamber and designate that chamber to dispense a particular medication. To this end, the user/caretaker would typically place a certain number of pills of that medication into the selected chamber and would enter the relevant information. This information may include the name of the medication, the number of pills placed in the chamber, the prescribed dosage and schedule, and the pill size. In some embodiments, the software can communicate with an FDA database, healthcare-provider database, and/or a pharmacy database and access information about the pill size, so the user/caretaker need not provide the size information. The software may also communicate with a medication prescriber's or provider's system (such as a server at the doctor's office or at a pharmacy), to obtain information about the dosage and schedule of a particular medication. The software app may also send or receive requests for additional dosage, in response to an action taken by a user such as clicking or tapping a button displayed by the app, and may display the corresponding messages. In these embodiments, the app would allow a caretaker to approve or deny such requests, and would transmit the caretaker action to the corresponding ICMD device.

Figure 8:
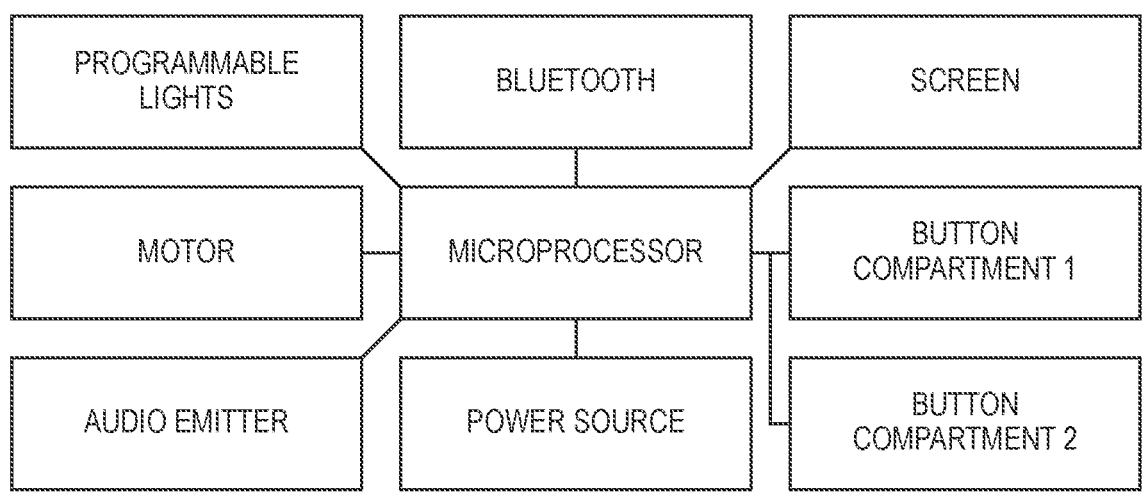
FIG. 8 schematically depicts various components of a pill-dispensing device, according to one embodiment.

In various embodiments, the ICMD device includes a microprocessor that is programmed to receive the information provided by the user/caretaker via their apps and/or the requests made by the user using the buttons, as shown in FIG. 8. The microprocessor is also programmed to communicate the results of an action taken or not taken to the LEDs, the LCD screen, and/or the user and caretaker apps. In addition, the microprocessor is programmed to control the motor that spins the spinning disc. In particular, the microprocessor would use the schedule and dosage information to determine the days and times at which the rotation of the motor should be activated so that pills from various chambers would be dispensed according to their respective schedules and dosages. To this end, the microprocessor may also select motor speeds as discussed above, e.g., to dispense pills from one or more chamber and to avoid dispensing pills from one or more chambers at a particular time. In addition, the microprocessor uses the information about the pill size and the sizes of the holes/openings in the non-moving enclosure disc and the hole in the spinning disc to determine the angle of rotation for each chamber, so that only one pill would be dispensed at a time from a selected chamber.

Software

The software component may include two different portals that can facilitate communication between the user and the caretaker, as well as to provide a system of checks and balances to ensure the safety of the consumer of the medication. These portals are called the user portal and the caretaker portal. In this context, a user is anyone using the ICMD device to take medications, and a caretaker can be anyone the user trusts with his or her medication information. Both the user and the caretaker can program the ICMD device, and the caretaker can receive and approve or deny requests for additional dosages.

As shown in FIG. 9, within the caretaker portal, the caretaker can view information regarding the medications being dispensed, or previous medications that have already been dispensed. Information about the date and time of the most recent consumption can be seen, and the caretaker can also see information about the next planned date/time at which the medication will be dispensed. Furthermore, the caretaker can see and/or program a schedule for the dispensing of one or more drugs.

The caretaker portal can also display logistical information such as the number of pills remaining in each chamber of the pill bottle. Some embodiments of the ICMD device do not include a sensor/counter that can count the number of pills remaining in each chamber of the bottle, but the software keeps an active log of the dispensed pills. Initially, the caretaker provides to the software the respective numbers of pills placed in each chamber of the pill bottle. The software decrements the respective counters as pills are dispensed from each chamber, providing both the caretaker and the user accurate counts of the pills remaining in each chamber of the bottle. In some embodiments, sensors and counters are contemplated for one or more chambers.

A log of all the patient's interactions with the pill bottle may be stored securely and can be presented to the caretaker. This log shows information such as the interaction type, the date of the interaction, and the medication name. The types of interactions may include acknowledgment that a dispensed pill was consumed, lack of such an acknowledgment, indicating missed dosages, and request for an additional dosage. Regardless of how the user interacts, i.e., using the buttons on the cap or via the user portal, the caretaker portal can obtain and provide the user interaction information to the caretaker. These logs allow the caretaker to make an accurate, informed decision regarding additional dosage requests from the user. Using the information provided to the caretaker via the log, the caretaker can look for signs of potential abuse, such as consistent requests for additional medication, and can act, such as by denying requests for that specific medication. Likewise, the caretaker can also see whether the patient has been consistently missing her medications, which may prompt the caretaker to approve the request and/or to take other actions, as needed.

Figures 10, 11:
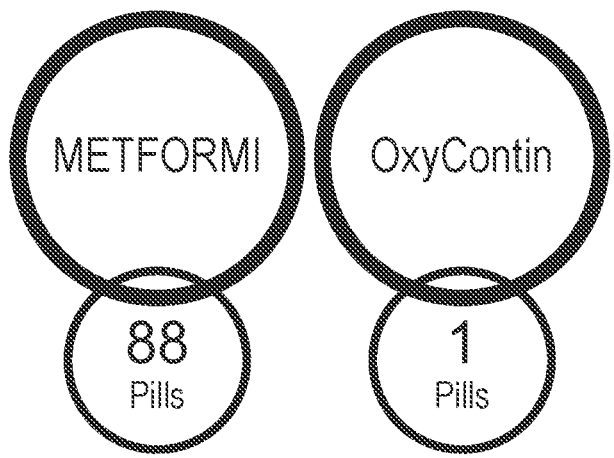
FIG. 10 illustrates the information displayed at a local user interface, according to one embodiment.
FIGS. 11-13 illustrate different types of information displayed at user interfaces, according to various embodiments.

In various embodiments, the software component also includes a user application/app/portal, shown in FIG. 10. The user portal may provide the same functions and/or information as the caretaker portal, except that user portal is not configured to provide approval for additional dosages. Each portal can be executed on a computer, such as a desktop, laptop, or a tablet, and/or on a mobile device such as a tablet, a smartphone, or a smart watch. FIG. 10 shows the two drugs that are stored in two chambers of the pill bottle, and also the number of remaining pills in each chamber.

Each portal provides one or more user interface (UI) buttons that allow the user and the caretaker to undertake various actions. For example, one button allows the user/caretaker to access activity logs. In addition, a set of buttons is provided where each button corresponds to a particular chamber of the pill bottle and displays the name of the medication stored in that chamber. When that button is pressed on a user app, a request is sent to the ICMD device and the corresponding medication may be dispensed if a validation check passes, i.e., if the caretaker approves the request. Another button or a set of buttons allows the user/caretaker to program the ICMD device to dispense a new medication or to renew the previously programmed dispensing of a particular medication. When a "new medication" button is pressed, a new medication screen, such as that shown in FIG. 11, is presented. On this screen the user or the caretaker can provide information such as the drug name, dosage, schedule, time period after which the missed dosage notification is triggered, and/or pill size.

Figures 12, 13:
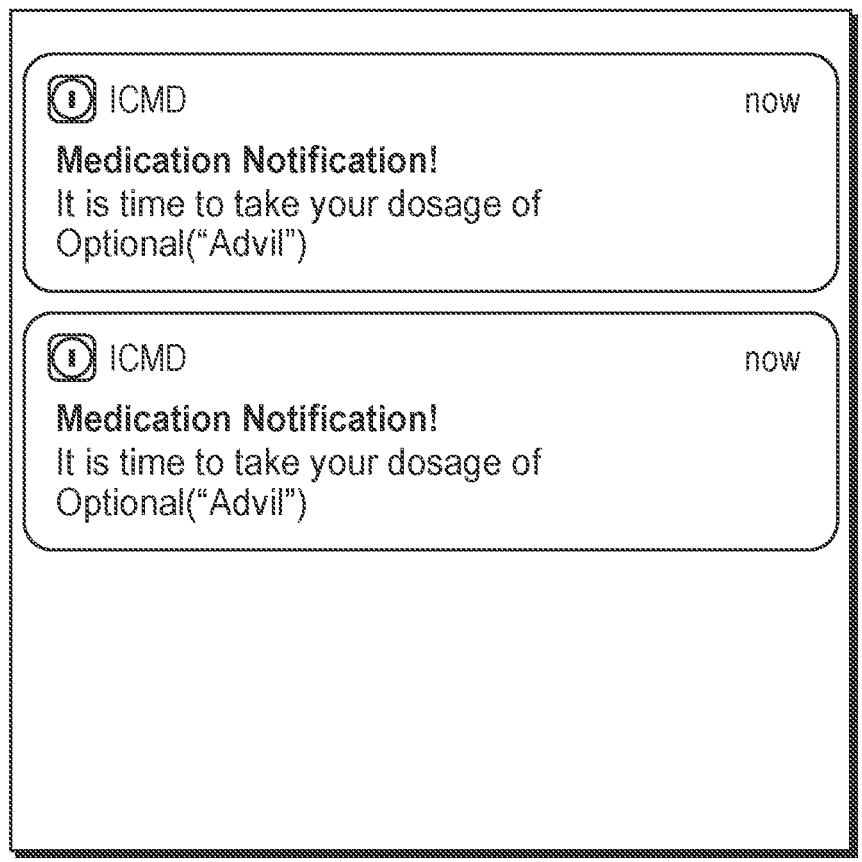

With reference to FIG. 12, in some embodiments, the user/caretaker can scan the drug label received from the pharmacy where, using the optical character recognition (OCR) technology available on a mobile device, the app itself determines the relevant information about the medication, such as the drug name, dosage, and schedule. To this end, the apps identify various keywords on the label, such as "daily," "weekly," "twice a day," etc., and use this information to create a schedule automatically for the user. This information is displayed so that the user/caretaker can confirm the accuracy of the information and/or may modify the information, as needed.

The user/caretaker may also supply additional information, such as time period after which the missed dosage notification is triggered, and/or pill size. In some embodiments, the time period to trigger missed dosage notification is the same for all medications, and may be entered only once. In some embodiments, the apps communicate with an external database, such as an FDA database, a healthcare provider database, a pharmacy database, etc., to obtain the pill size. The apps may also communicate with the pharmacy database or a server at the doctor's office to obtain the dosage and schedule information for a particular drug.

In some embodiments, after a drug name is provided, either manually or via scanning/OCR, the app retrieves certain safety information from the external databases about that drug so as to provide safety instructions to the user/caretaker. For example, a certain non-prescription drug may be unsuitable for persons with a certain medical condition, such as hypertension, and who are prescribed another medication for that condition. The ICMD device can alert the user/caretaker if the device is programmed to dispense that other medication. In other cases, warnings regarding the dangers of consuming a medication (such as Oxycodone™) with alcohol, or recommendation to take a particular drug with food, can be presented. These warnings can be presented to the user via the LCD screen and/or on the app screen.

In addition, when the time to dispense a drug approaches, e.g., when the drug would be dispensed after a selected time period such as 10 min, 15 min, half an hour, etc., the app may provide a notification, as shown in FIG. 13. The user and/or the caretaker can program/specify this time period. Notifications may also be provided by the app when the drug is dispensed, and when the user does not acknowledge taking a dispensed drug within a preset time. The notification may include displaying a message, as shown in FIG. 13 and/or sounding an alarm or a chime on a computer/device running the app.

In various embodiments, the scanning/OCR and database-based retrieval of information can minimize the user's or caretaker's effort in programming the ICMD device, and can also minimize errors in entering drug information, dosages, and schedules. Tus, the system of checks and balances facilitated by the two-portal software system can promote a strict compliance with the drug prescriptions.

Network Architecture

Figure 14:
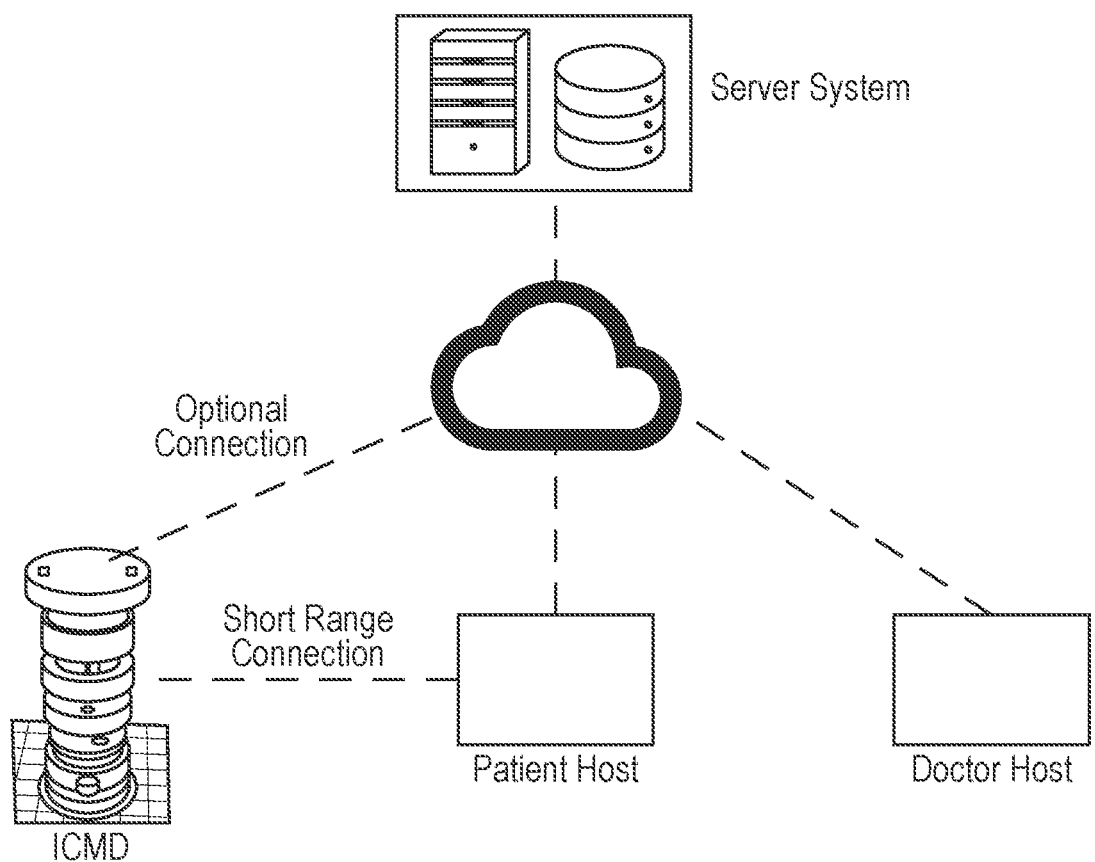
FIG. 14 schematically depicts communications between various computing systems and a pill-dispensing device, according to one embodiment.

Various embodiments of the ICMD system rely on a peer-to-peer (P2P) network architecture. With reference to FIG. 14, the network architecture includes several nodes such as an ICMD device, a central server/database, a user app, a caretaker app (not shown), a doctor's system, and external databases (not shown) such as a pharmacy database, FDA database, etc. Via communications between the nodes of the ICMD network, the system of checks and balances that is described above can be implemented. This can also improve the reliability and accuracy of medication consumption.

The central server/database contains information relevant to each ICMD device that is managed by the server. Although FIG. 14 shows only one ICMD device node, only one user app node, etc., one central/server can manage several nodes of each of the other types. Because medical information is stored in the database, the server system is generally compliant with Health Insurance Portability and Accountability Act (HIPAA), in various embodiments. The server may be hosted remotely, in a private cloud, or may be provided using a public cloud such as Amazon® Web Services (AWS®), Microsoft® Azure® platform, etc. In some embodiments, the database is encrypted and hashed, e.g., in accordance with the HIPAA standards, and the user and caretaker apps and the respective data they store are also encrypted and hashed.

The central server/database system stores information about the state of each ICMD device the central server/database manages. This information may include any and all of the information associated with the drugs to be dispensed by the managed ICMD devices, such the total number of chambers in a particular ICM device, the number of occupied chambers in that device, the names of the medications in the different chambers, the dosages and schedules of those medications, the number of pills placed and/or remaining in each chamber, etc. The database schema can uniquely identify which medication is in which chamber of a particular ICMD device. This information can be securely queried by the other nodes of the network, such as by the user app and the caretaker app. The information can only be accessed by an authorized node. For example, information associated with the ICMD device used by "Person X" is accessible only to the apps associated with Person X and the designated caretaker of Person X. Likewise, information associated with the ICMD device used by "Person Y" is accessible only to the apps associated with Person Y and the designated caretaker of Person Y.

The node corresponding to the user app can communicates directly with the ICMD device and with the central server/database, either directly or through a network. Direct communication between the user app and the ICMD device may be facilitated using a close proximity communication protocol such as Bluetooth™, Near Field Communication (NFC) protocol, etc. The user app can both query information from and supply information to the central server/database. Information is supplied when the user programs an ICMD device to dispense a drug or renews a previously entered dispensing schedule. Similarly, the caretaker app can also query information from and supply information to the central server. A request for an additional dosage may be transmitted from the ICMD device or the user app to the central server. The server would then forward the request to the caretaker app, and receive a response (i.e., approval or denial of the request). The server can then communicate with the ICMD device directly or via the user app, e.g., to dispense the additional dosage or to display a message that the request was denied.

It is clear that there are many ways to configure the device and/or system components, interfaces, communication links, and methods described herein. The disclosed methods, devices, and systems can be deployed on convenient processor platforms, including network servers, personal and portable computers, and/or other processing platforms. Other platforms can be contemplated as processing capabilities improve, including personal digital assistants, computerized watches, cellular phones and/or other portable devices. The disclosed methods and systems can be integrated with known network management systems and methods. The disclosed methods and systems can operate as an SNMP agent, and can be configured with the IP address of a remote machine running a conformant management platform. Therefore, the scope of the disclosed methods and systems are not limited by the examples given herein, but can include the full scope of the claims and their legal equivalents.

The methods, devices, and systems described herein are not limited to a particular hardware or software configuration, and may find applicability in many computing or processing environments. The methods, devices, and systems can be implemented in hardware or software, or a combination of hardware and software. The methods, devices, and systems can be implemented in one or more computer programs, where a computer program can be understood to include one or more processor executable instructions. The computer program(s) can execute on one or more programmable processing elements or machines, and can be stored on one or more storage medium readable by the processor (including volatile and non-volatile memory and/or storage elements), one or more input devices, and/or one or more output devices. The processing elements/machines thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processing element as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. Sets and subsets, in general, include one or more members.

As provided herein, the processor(s) and/or processing elements can thus be embedded in one or more devices that can be operated independently or together in a networked environment, where the network can include, for example, a Local Area Network (LAN), wide area network (WAN), and/or can include an intranet and/or the Internet and/or another network. The network(s) can be wired or wireless or a combination thereof and can use one or more communication protocols to facilitate communication between the different processors/processing elements. The processors can be configured for distributed processing and can utilize, in some embodiments, a client-server model as needed. Accordingly, the methods, devices, and systems can utilize multiple processors and/or processor devices, and the processor/processing element instructions can be divided amongst such single or multiple processor/devices/processing elements.

The device(s) or computer systems that integrate with the processor(s)/processing element(s) can include, for example, a personal computer(s), workstation (e.g., Dell, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a processor", or "a processing element," "the processor," and "the processing element" can be understood to include one or more microprocessors that can communicate in a stand-alone and/or a distributed environment(s), and can thus can be configured to communicate via wired or wireless communication with other processors, where such one or more processor can be configured to operate on one or more processor/processing elements-controlled devices that can be similar or different devices. Use of such "microprocessor," "processor," or "processing element" terminology can thus also be understood to include a central processing unit, an arithmetic logic unit, an application-specific integrated circuit (IC), and/or a task engine, with such examples provided for illustration and not limitation.

Furthermore, references to memory, unless otherwise specified, can include one or more processor-readable and accessible memory elements and/or components that can be internal to the processor-controlled device, external to the processor-controlled device, and/or can be accessed via a wired or wireless network using a variety of communication protocols, and unless otherwise specified, can be arranged to include a combination of external and internal memory devices, where such memory can be contiguous and/or partitioned based on the application. For example, the memory can be a flash drive, a computer disc, CD/DVD, distributed memory, etc. References to structures include links, queues, graphs, trees, and such structures are provided for illustration and not limitation. References herein to instructions or executable instructions, in accordance with the above, can be understood to include programmable hardware.

Although the methods and systems have been described relative to specific embodiments thereof, they are not so limited. As such, many modifications and variations may become apparent in light of the above teachings. Many additional changes in the details, materials, and arrangement of parts, herein described and illustrated, can be made by those skilled in the art. Accordingly, it will be understood that the methods, devices, and systems provided herein are not to be limited to the embodiments disclosed herein, can include practices otherwise than specifically described, and are to be interpreted as broadly as allowed under the law.

What is claimed is:

1. A device for dispensing medication pills, the device comprising:
   a first chamber for storing a first type of pills, the first chamber having an inlet;
   a nonmoving enclosure disk enclosing the first chamber and having a first hole independent of size and shape of the pills of the first type, and providing an outlet from the first chamber;
   a rotatable disk coupled to a motor and having a dispensing hole alignable with the first hole in the enclosure disk; and
   a local controller for initiating a rotation of the rotatable disk and for controlling an angle of rotation of the rotatable disk such that at a first angle of rotation used by the local controller an overlap between the first hole in the enclosure disk and the dispensing hole in the rotatable disk corresponds to a size of a pill of the first type.

2. The device of claim 1, wherein the inlet of the first chamber comprises a spring-loaded lid.

3. The device of claim 1, wherein the local controller is programmed to initiate the rotation of the rotatable disk according to one or more of: a first time of the day, a first frequency of dispensing pills of the first type, or an administer override.

4. The device of claim 1, further comprising a second chamber for storing a second type of pills, the second chamber having an inlet, wherein:
   the enclosure disk encloses the second chamber and has a second hole providing an outlet from the second chamber;
   the dispensing hole of the rotatable disk is alignable with the second hole in the enclosure disk; and
   the local controller is configured for controlling the angle of rotation of the rotatable disk such that at a second angle of rotation used by the local controller an overlap between the second hole in the enclosure disk and the dispensing hole in the rotatable disk corresponds to a size of a pill of the second type.

5. The device of claim 4, wherein the inlet of the second chamber comprises a spring-loaded lid.

6. The device of claim 4, wherein the local controller is programmed to initiate the rotation of the rotatable disk according to one or more of: a second time of the day, a second frequency of dispensing pills of the second type, or an administer override.

7. The device of claim 4, wherein the local controller is programmed to cause a rotation of the rotatable disk while the dispensing hole passes over the first hole in the enclosure disk at an angular speed at which a pill is not dispensed through the first hole and the dispensing hole when the first hole in the enclosure disk and the dispensing hole are aligned.

8. The device of claim 1, wherein the local controller comprises:
   a processor; and
   a communication interface for receiving one or more of a set of control parameters or a set of instructions, for programming the local controller.

9. The device of claim 8, wherein:
   the set of control parameters comprises one or more of: a pill identifier; a pill type, a set of one or more times of the day at which a pill of a specified type is to be dispensed, a frequency of dispensing pills of the specified type, or a size of a pill of the specified type; and
   the processor is programmed to compute the first angle of rotation based on, at least in part, the size of the pill of the specified type.

10. The device of claim 9, wherein:
    the pill identifier is specified via the communication interface;
    the pills of the specified type comprise pills identified by the pill identifier; and
    the local controller is programmed to:
    query a database using the pill identifier; and
    determine, using information received from the database, one or more of: (i) the set of one or more times of the day at which a pill of the specified type is to be dispensed, (ii) the frequency of dispensing pills of the specified type, and (iii) the size of a pill of the specified type.

11. The device of claim 8, wherein:
    the set of instructions comprises a schedule for initiation of rotation of the rotatable disk; and
    the set of control parameters comprises the first angle of rotation.

12. The device of claim 8, wherein the communication interface is adapted to receive one or more of: a user acknowledgment that a dispensed pill was consumed, or a user request to dispense a pill of the first type.

13. The device of claim 12, wherein, upon receiving the user request to dispense a pill, the communication interface is programmed to seek authorization prior to dispensing the pill.

14. The device of claim 1, further comprising an alarm configured to indicate one or more conditions comprising:
    a time at which a pill of the first type would be dispensed is approaching;
    a pill of the first type has been dispensed; or
    a user-specified time has elapsed after a pill of the first type was dispensed.

15. The device of claim 1, wherein the first type of pills is selected from the group consisting of: opioids, prescription medication; or non-prescription medication.

16. A user device comprising a remote controller in electronic communication with a local controller of a pill-dispensing device comprising a pill chamber, a nonmoving enclosure disk, and a motorized rotatable disk, wherein:

the local controller is programmed to initiate a rotation of the rotatable disk relative to the nonmoving enclosure disk having a first hole independent of size and shape of the pills of the first type, according to one or more of: a time of the day at which a pill is to be dispensed, a frequency of dispensing pills, a pill size, a total number of pills initially placed in the chamber, a pill identifier, or an administer override; and the remote controller is programmed to transmit to the local controller one or more of: the time of the day at which the pill is to be dispensed, the frequency of dispensing pills, the pill size, the total number of pills initially placed in the chamber, or the pill identifier.

17. The user device of claim 16, wherein the remote controller is further programmed to:

receive from the local controller of the pill-dispensing device an authorization request for dispensing a pill;

provide, in response to the received request, a signal to a user; and transmit, according to a user input, the administer override to the local controller.

18. The user device of claim 16, wherein the remote controller is further programmed to:

receive from the local controller of the pill-dispensing device information about dispensing of pills, the information comprising one or more of: a number of pills dispensed during a specified time period, a number of pills remaining in the chamber, a number of authorization requests for dispensing the pill, or the number of administer overrides; and display the received information.

19. A method for dispensing medication pills, the method comprising the steps of:

initiating, at a pre-selected first time and according to a first angle of rotation, a rotation of a rotatable disk of a medical pill dispensing device, causing at the first angle of rotation an overlap between a first hole in a nonmoving enclosure disk of the medical pill dispensing device and a dispensing hole in the rotatable disk, the first hole in the nonmoving enclosure disk being independent of size and shape of the pills of the first type;

limiting a speed of rotation such that a medical pill of a first type is dispensed from the device when the first hole in the enclosure disk and the dispensing hole in the rotatable disk are aligned; and stopping the rotation of the rotatable disk after the dispensing hole in the rotatable disk passes over the first hole in the enclosure disk.

20. The method of claim 19, further comprising:

initiating, at a pre-selected second time and according to a second angle of rotation, a rotation of the rotatable disk of the medical pill dispensing device, causing at the second angle of rotation an overlap between a second hole in the enclosure disk of the medical pill dispensing device and the dispensing hole in the rotatable disk;

limiting a speed of rotation such that a medical pill of a second type is dispensed from the device when the second hole in the enclosure disk and the dispensing hole in the rotatable disk are aligned; and stopping the rotation of the rotatable disk after the dispensing hole in the rotatable disk passes over the second hole in the enclosure disk.

21. The method of claim 19, wherein:

at a second angle of rotation, the dispensing hole in the rotatable disk is aligned with a second hole in the enclosure disk; and maintaining the speed of rotation such that a medical pill of the second type is prevented from being dispensed from the device when the second hole in the enclosure disk and the dispensing hole in the rotatable disk are aligned.

22. The method of claim 19, further comprising:

repeating the initiating, limiting, and stopping steps at a pre-selected third time such that another medical pill of the first type is dispensed from the device at the third time.

23. A method for controlling dispensing of medication pills from a pill-dispensing device having at least one pill chamber, each chamber being designated to a particular type of pills, the method comprising the steps of:

receiving a first chamber identifier, identifying a first chamber designated for storing medication pills of a first type, the first chamber being enclosed by a nonmovable enclosure disk having a first hole corresponding to the first chamber;

obtaining a size of the pills of the first type;

computing a first angle of rotation for a rotatable disk of the pill-dispensing device, the first angle being relative to a specified origin of the rotatable disk and being based on: (i) a total number of chambers in the device, (ii) the first chamber identifier, and (iii) the size of the pills of the first type, so that an area of overlap between the first hole in the enclosure disk and a dispensing hole in the rotatable disk corresponds to the size of the pills of the first type; and selecting an angular speed of rotation for the rotatable disk when the rotatable disk is rotated through the first angle.

24. The method of claim 23, wherein the size of the pills of the first type comprises at least one of a length of the pill, a width of the pill, or a diameter or the pill.

25. The method of claim 23, wherein obtaining the size of the pills of the first type comprises receiving the size of the pills of the first type.

26. The method of claim 23, wherein obtaining the size of the pills of the first type comprises:

receiving a first pill identifier identifying the pills of the first type; and accessing a database using the first pill identifier and receiving from the database the size of the pills of the first type.

27. The method of claim 23, wherein the steps of receiving, obtaining, computing, and selecting are performed at a remote controller, the method further comprising:

transmitting the first angle of rotation and the angular speed of rotation to a local controller included in the pill-dispensing device.

28. The method of claim 23, wherein the steps of obtaining the size of the pills of the first type is performed at a remote controller, the method further comprising:

transmitting the size of the pills of the first type to a local controller included in the pill-dispensing device.

29. The method of claim 23, further comprising:
receiving a second chamber identifier, identifying a second chamber designated for storing medication pills of a second type, second chamber being enclosed by the nonmovable enclosure disk, wherein the enclosure disk has a second hole corresponding to the second chamber;
obtaining a size of the pills of the second type; and
computing a second angle of rotation for the rotatable disk of the pill-dispensing device, the second angle being relative to the specified origin of the rotatable disk and being based on: (i) the total number of chambers in the device, (ii) the second chamber identifier, and (iii) the size of the pills of the second type, so that an area of overlap between the second hole in the enclosure disk and the dispensing hole in the rotatable disk corresponds to the size of the pills of the second type.

30. The method of claim 23, wherein:
the selected angular speed of rotation allows dispensing of the pill from the pill-dispensing device; or
the selected angular speed of rotation prevents dispensing of the pill from the pill-dispensing device.

\* \* \* \* \*